(12) United States Patent
Reunanen et al.

(10) Patent No.: US 8,023,720 B2
(45) Date of Patent: Sep. 20, 2011

(54) METHOD AND APPARATUS FOR IDENTIFYING REPEATED PATTERNS

(75) Inventors: Juha Reunanen, Helsinki (FI); Antti Saarela, Vihti (FI)

(73) Assignee: ABB Oy, Helsinki (FI)

( * ) Notice: Subject to any disclaimer, the term of this patent is extended or adjusted under 35 U.S.C. 154(b) by 1140 days.

(21) Appl. No.: 11/808,118

(22) Filed: Jun. 6, 2007

(65) Prior Publication Data
US 2007/0286472 A1  Dec. 13, 2007

(30) Foreign Application Priority Data
Jun. 13, 2006  (EP) ..................................... 06012084

(51) Int. Cl.
G06K 9/00  (2006.01)
(52) U.S. Cl. ........................................ 382/141; 382/209
(58) Field of Classification Search .................... 382/141
See application file for complete search history.

(56) References Cited

U.S. PATENT DOCUMENTS

| | | | | |
|---|---|---|---|---|
| 4,675,730 A * | 6/1987 | Adomaitis et al. ............ | 348/131 |
| 4,701,859 A * | 10/1987 | Matsuyama et al. .......... | 382/144 |
| 4,828,156 A * | 5/1989 | Whiteley et al. .................. | 226/1 |
| 4,951,223 A * | 8/1990 | Wales et al. ...................... | 702/40 |
| 4,958,307 A * | 9/1990 | Nishimura ..................... | 382/141 |
| 5,046,109 A * | 9/1991 | Fujimori et al. ............... | 382/144 |
| 5,068,799 A * | 11/1991 | Jarrett, Jr. ....................... | 702/40 |
| 5,146,311 A | 9/1992 | Chang | |
| 5,301,129 A * | 4/1994 | McKaughan et al. ......... | 382/149 |
| 5,305,392 A * | 4/1994 | Longest et al. ................ | 382/112 |
| 5,436,979 A * | 7/1995 | Gray et al. ..................... | 382/141 |
| 5,440,648 A * | 8/1995 | Roberts et al. ................ | 382/141 |
| 5,583,950 A * | 12/1996 | Prokoski ........................ | 382/212 |
| 5,631,981 A | 5/1997 | Rao | |
| 5,774,177 A * | 6/1998 | Lane ................................ | 348/88 |
| 5,859,698 A * | 1/1999 | Chau et al. .................. | 356/237.2 |
| 5,864,394 A | 1/1999 | Jordan, III et al. | |
| 6,031,931 A * | 2/2000 | Chiu et al. ..................... | 382/141 |
| 6,100,989 A * | 8/2000 | Leuenberger ................. | 356/430 |
| 6,222,936 B1 * | 4/2001 | Phan et al. ..................... | 382/149 |
| 6,236,429 B1 * | 5/2001 | Ho .................................. | 348/88 |
| 6,266,437 B1 * | 7/2001 | Eichel et al. .................. | 382/149 |
| 6,366,358 B1 * | 4/2002 | Satou et al. .................. | 358/1.14 |

(Continued)

FOREIGN PATENT DOCUMENTS

WO  02/078873 A1  10/2002

OTHER PUBLICATIONS

European Search Report dated Dec. 12, 2006.

*Primary Examiner* — Sath V Perungavoor
(74) *Attorney, Agent, or Firm* — Buchanan Ingersoll & Rooney PC

(57) ABSTRACT

In an exemplary method, repeated patterns are identified in a strip-like product. In the method the strip-like product is observed by at least one camera, and at least one digital image signal comprised of pixels is created for inspection. The image signal is searched for anomalies comprised of one or more pixels. A search image is created of any detected anomaly and its neighbourhood, and the search image is used to convolute the image signal being examined, creating a response image signal. The response image signal is used to determine image areas in the image signal being examined that are substantially similar to the search image.

9 Claims, 5 Drawing Sheets

U.S. PATENT DOCUMENTS

| | | | |
|---|---|---|---|
| 6,407,373 B1* | 6/2002 | Dotan | 250/201.3 |
| 6,539,106 B1* | 3/2003 | Gallarda et al. | 382/149 |
| 6,542,240 B2* | 4/2003 | Lagace | 356/429 |
| 6,750,466 B2* | 6/2004 | Guha et al. | 250/559.46 |
| 6,909,798 B1* | 6/2005 | Yukawa et al. | 382/141 |
| 7,065,239 B2* | 6/2006 | Maayah et al. | 382/145 |
| 7,297,969 B1* | 11/2007 | Wolinsky et al. | 250/548 |
| 7,366,343 B2* | 4/2008 | Takeuchi | 382/145 |
| 7,797,133 B2* | 9/2010 | Floeder et al. | 702/183 |
| 2001/0031079 A1 | 10/2001 | Ryder | |
| 2002/0105618 A1* | 8/2002 | Edgar et al. | 352/38 |
| 2002/0110269 A1* | 8/2002 | Floeder et al. | 382/141 |
| 2003/0053675 A1* | 3/2003 | Kuwabara | 382/145 |
| 2003/0076989 A1* | 4/2003 | Maayah et al. | 382/145 |
| 2003/0228050 A1* | 12/2003 | Geshel et al. | 382/149 |
| 2004/0086168 A1* | 5/2004 | Kuwabara | 382/145 |
| 2004/0126909 A1* | 7/2004 | Obara et al. | 438/14 |
| 2005/0075801 A1* | 4/2005 | Skeps et al. | 702/35 |
| 2006/0280358 A1* | 12/2006 | Ishikawa | 382/149 |
| 2007/0286472 A1* | 12/2007 | Reunanen et al. | 382/143 |
| 2010/0063750 A1* | 3/2010 | Floeder et al. | 702/35 |

* cited by examiner

METHOD AND APPARATUS FOR IDENTIFYING REPEATED PATTERNS

RELATED APPLICATIONS

This application claims priority under 35 U.S.C. §119 to EP Application 06012084 filed in Europe on Jun. 13, 2006, the entire contents of which are hereby incorporated by reference in their entireties.

TECHNICAL FIELD

A method and an apparatus are disclosed for identifying repeated patterns in a strip-like product.

BACKGROUND INFORMATION

Repeated fault patterns in strip-like products are usually caused by faults in or erroneous operation of machine elements. For example, repeated faults will arise in the process of metal band rolling if there is a fault or anomaly in the working roll, causing it to imprint the final product at regular intervals. Correspondingly, in the process of paper manufacturing, faults in the rolls or incorrect operation of the calendar will cause repeated variations in paper quality. A roll generally refers to an approximately cylindrical machine element that is in contact with a strip-like product and rotates in the direction in which the product progresses. It must be noted that the roll may rotate at a speed different from the speed of the product.

In some cases one or more missing patterns within a regularly repeated pattern are considered a fault in a strip-like product. These include, for example, a watermark missing from watermarked paper or an imprint missing from printed adhesive paper.

Even if weak, such a cyclical fault is often more severe than an individual fault from the point of view of the metal roller or paper-maker, as well as the end client.

Automatic visual inspection of the surface of strip-like products is often based on CCD line scan cameras that take pictures of light reflected from the surface of the product at different angles. The web itself is moving, so an image can be created by reading a single line at a time at a high speed. The image signal from the CCD line camera is converted to a digital format and digitally processed in an image-processing unit. The end product of the process is a set of electronic images representing selected parts of the strip-like product.

The publication WO 02/078873 A1 presents a method for detecting a faulty roll in the manufacture of a strip-like product. The strip is inspected after the roll unit for any visual faults, and when one is detected the faulty roll is located by opening and closing roll pairs under timed control.

The publication U.S. Pat. No. 4,958,307 presents an apparatus for inspecting regular roll marks. The apparatus stores imprint data along the diameter of the roll into memory and compares the imprint data with reference data at each full revolution of the roll.

SUMMARY

A method and an apparatus are disclosed for identifying repeated patterns in a strip-like product.

In an exemplary method, repeated patterns are identified in a strip-like product. In the method the strip-like product is observed by at least one camera, and at least one digital image signal comprised of pixels is created for examination. The image signal is searched for anomalies comprised of one or more pixels. A search image is created of any detected anomaly and its neighborhood, and the search image is used to convolute the image signal being examined, creating a response image signal. The values of the response image signal are used to determine image areas in the image signal being examined that are substantially similar to the search image.

In an exemplary apparatus for identifying repeated patterns in a strip-like product, the strip-like product is observed by at least one camera. The apparatus creates at least one digital image signal comprised of pixels for examination. The apparatus includes means for searching the image signal for an anomaly comprised of one or more pixels and means for creating a search image of any detected anomaly and its neighborhood. The apparatus includes means that can be used to convolute the image signal being examined with the search image, means for creating a response image signal from the convolution, and means for determining image areas in the image signal being inspected that are substantially similar to the search image.

In an exemplary method, a long image can also be determined from the image signal. The length of the image is determined on the basis of the object so that several occurrences of a fault can be included in the image. The image signal comprises lines of pixels arranged by time, created by exposure of a moving strip-like product. The camera sensor comprises several light-sensitive elements, and the neighborhood relations of the data pixels produced by the sensors correspond to the neighborhood relations of the sensor elements. When the image is created the lines of pixels are arranged in the same fashion as they were at the moment of imaging. The image can be created one line at a time or from consecutive images. The image signal is digital—that is, an image expressed numerically. For example, in the case of rolling a metal band, each pair of roller units makes the metal band thinner. This causes the band to elongate, which extends the recurrence interval of repeated faults. Such thinning is taken into account in accordance with the longest interval of thinning, for example. A long image must accommodate at least three revolutions of the roll so that it will include at least two cycles of a fault pair.

The image or image signal taken of the object is searched for anomalies. An anomaly is an area that is visually different from the appearance of the image. For example, an anomalous pixel can be searched by comparing its value with fixed analogue or digital limits. A pixel will be characterized as an anomaly if its value is over a maximum limit or under a minimum limit. On the other hand, anomalous pixels can be chosen on the basis of excessive darkness or lightness in a high-pass filtered image signal. This is used to create a binary image of the anomalous areas, and one area at a time is picked as a suspected repeated fault. The image signal values surrounding the suspected fault area are copied to create a search image.

After this, similar anomalies are searched for at each point in the cross direction. The anomalous areas are convoluted with the search image in the longitudinal direction of the strip-like product—that is, in the machine direction. An area—also known as the search image—cut from the image signal or image is slid in the machine direction and slightly in the cross direction, searching for areas that are as similar to the cut area as possible. Slight sliding in the cross direction allows the track to move during the creation of the image signal, for example. The similarity measure can be any correlation measure between the original finding and the other sections. A correlation measure can be comprised of the derivatives of convolution using different normalization factors. If similar areas are located at regular intervals in the object, the phenomenon is regularly repeating.

When separate areas of the image have been determined to represent the same repeated fault, a resulting image of a good quality—also known as a model image—can be created by aligning the partial images and calculating a pixel-wise median, for example. Such an image will emphasize the actual interesting repeated phenomenon, such as a fault, but efficiently suppress any random spots and other non-repeated factors that hamper the detection of a weak fault.

The method and apparatus are able to detect repeated faults that are weak enough to be insignificant at the time of detection. Great accuracy enables these faults to be monitored and action to be taken before they develop into faults that would cause actual problems.

According to an embodiment, the method and apparatus enable quick detection of regularly repeated faults in a product and the identification of their source. This will improve the quality of the final product and minimize downtime of the production plant. Different occurrences of the same regularly repeated anomaly are always repeated in the image signal created of the inspected object as approximately similar and at regular intervals.

When using the exemplary method for finding missing patterns within a regularly repeated pattern, it is advantageous but not necessary for the method to carry out convolution with the search image twice. At the first stage the exact intervals of recurrence of the repeated pattern in the longitudinal and cross direction are determined. On the basis of this, an ideal image is created with the intention of minimizing the effect of noise and background variations. During the second stage of convolution this ideal image is used as the search image. When this is done it is economical but not necessary for the method to limit the first phase of convolution using search images determined from the anomalous areas to convolute with only a few search images. Deviating from the search for a repeated phenomenon, convolution is carried out using each selected search image over the entire width of the image signal or cut image in the cross direction. Convolution in the longitudinal direction is carried out over the entire selected image signal area or cut image. When selecting a few search images the selection can be made at random among the anomalous areas or by selecting the ten greatest anomalous areas, for example. Because it is assumed that the image signal or image contains a regularly repeated pattern, the selection of the search image and its exact size are not very significant as long as the search image includes large parts of the regularly repeated pattern. This can be ensured by cutting a part of the image signal or image to serve as the search image that is at least equal in size to the repeating interval if the maximum length of the repeating interval of a regularly repeated pattern in the longitudinal and cross direction is known in advance. Response images are created by convolution with the selected search images. Similar image areas are determined from the response images, and the distances between the image areas are determined in the longitudinal and cross direction. The distances are rounded to a suitable precision (such as 1 mm), and the most common longitudinal and cross-directional distances are selected among the rounded distances. These are the repeating intervals of the regularly repeated pattern in the corresponding directions. The known repeating intervals are used to cut partial images from the image signal or image that are sequential in the longitudinal and cross direction and equal in size to the repeating intervals. The partial images can be used to create an ideal image in which background variation is efficiently suppressed and the repeated pattern is emphasized in relation to measurement noise and background variation. This is done by aligning the cut images accurately on top of each other, for example by using the correlation measures referred to above, and by determining the value of each pixel in the ideal image by calculating the median of corresponding pixel values over the partial images, for example. The resulting ideal image is used to convolute over the image signal or image in the longitudinal and cross direction to create a new response image. Similar areas are determined from the resulting response image.

Once the method or apparatus has identified substantially similar image areas, the distances between them are calculated in the cross and longitudinal directions of the strip-like product. Longitudinal calculation can utilize information about the speed of the strip-like product at the time of imaging. On the other hand, cross-directional calculation can utilize information about any cross-directional movement of the track at the time of imaging.

The distance is a line between two detected anomalies. Its length is the distance between the end points of the line. The length of the distance in the machine direction or longitudinal direction is the length of the machine-direction component of the distance line. Correspondingly, the length of the distance line in the cross direction is the length of the cross-direction component of the distance line. The length of the distance line will hereafter refer to the length of the distance line in the machine or cross direction. A pair of distance lines comprises two distance lines, both of which are substantially either longitudinal or cross-directional. The distance between the lines in a distance line pair is defined as the smallest distance between the ends of the lines in the machine or cross direction. Therefore, for example, three occurrences of a repeated fault that are sequential in the machine direction and located at equal points in the cross direction constitute two distance lines that are sequential in the machine direction and have a mutual distance of zero in the machine direction. In this context the distance between distance line pairs refers to either the machine-direction or the cross-direction component of the distance.

The calculated distance lines are compared with each other, and distance lines that are substantially equal in machine-direction length and/or distance lines having lengths that are substantially multiples of each other are selected. The selected distance line pairs are used to create one or more distance line pairs consisting of two longitudinal distance lines. Furthermore, among the created distance line pairs, distance line pairs with a mutual distance in the machine direction substantially corresponding to a multiple of the machine-direction length of the shorter line in the pair are selected. The machine-direction distance between the lines in the selected distance line pairs can also be substantially zero—that is, the distance lines are sequential in the machine direction. After this, distance line pairs with the distance lines substantially close to each other in the cross direction of the strip-like product are selected from among these distance line pairs. The selected distance line pairs and the image areas at their ends constitute a regularly repeated pattern.

One exemplary embodiment is identifying repeated patterns in watermarked paper or printed adhesive paper, for example; in this case the intention is to search for a missing regularly repeated pattern. The manufacture of watermarked paper usually employs a watermark roll in which a metal mould corresponding to the pattern impresses the watermark on wet paper in the paper machine. Various faults in the roll, such as contamination or damage, will cause a defective repeated watermark pattern. In this case the apparatus and method are used for the quality control of a product having a repeated pattern. If one or more repeated patterns are found to be missing, this is considered to be an anomaly. An anomaly is searched for among identified substantially similar image areas by determining distance lines between the image areas in the cross and longitudinal direction of the strip-like product using calculatory methods and comparing the calculated distance lines with each other. In this case distance lines are only created between closely neighboring areas that are substantially aligned in the longitudinal or cross direction. Thus a maximum of four distance lines are determined for each image area, one in each longitudinal and cross direction. These distance lines are compared with each other, and the most common length of distance line present in the image is selected in the vertical and cross direction. After this, distances corresponding to multiples of the lengths of the selected distance lines are searched for in the vertical and cross direction correspondingly. The multiples of the distances found and the image areas between them constitute a pattern missing from a regularly repeated pattern.

An individual missing pattern located in the centre of the image produces two findings with a substantially equal centre point, in which case one of the findings can be ignored. On the other hand, the distance lines found will directly indicate the area and location of a missing pattern in the image, and this information can be utilized for reporting. The method is also able to detect cases in which an entire row or column of repeated patterns is missing from the image signal or image, or in which a row or column has shifted to the wrong place in terms of the regularly repeated pattern.

For example, in the manufacture of metal band, steel is made thinner using paired cylindrical rolls between which the metal band is conducted. If a piece of steel goes through the roll, it will create a dent in the roll that will impress a bump in the steel band at each revolution of the circumference of the roll when the dent contacts the metal band. Correspondingly, if something is stuck on the roll, the roll will impress a dent on the steel band at each revolution of the roll when the extra particles contact the metal band. On the other hand, simple wear of the roll will cause slight changes of level in the metal band. In this case the distance between three sequential anomalies detected using the method and apparatus can be used to determine the faulty working roll or several working rolls on the basis of their known circumference.

When information about the diameters of the working rolls and the amount of thinning at each pair of roll units is combined with fault detection information, the source of a detected repeated fault can be estimated using the following equation:

$$P_{final} = P_n \left(\frac{h_{1,F_{n+1}}}{h_{2,F_{n+1}}}\right)\left(\frac{h_{1,F_{n+2}}}{h_{2,F_{n+2}}}\right)\left(\frac{h_{1,F_{n+3}}}{h_{2,F_{n+3}}}\right)\cdots \left(\frac{h_{1,F_{n+i}}}{h_{2,F_{n+i}}}\right)$$

$$= P_n \left(\frac{h_{1,F_{n+1}} h_{1,F_{n+2}} h_{1,F_{n+3}} \cdots h_{1,F_{n+i}}}{h_{2,F_{n+1}} h_{2,F_{n+2}} h_{2,F_{n+3}} \cdots h_{2,F_{n+i}}}\right),$$

In which $P_{final}$ is the detected cycle of a repeated fault in the final product after going through i pairs of roll units, $P_n$ is the original cycle of the repeated fault caused by pair n of roll units, $h_{1,F_{n+i}}$ is the input thickness to the $i^{th}$ next pair of roll units and $h_{2,F_{n+i}}$ is the output thickness from the $i^{th}$ next pair of roll units. In other words, $h_{1,F_{n+i}}/h_{2,F_{n+i}}$ is the elongation in a pair of roll units.

The original cycle of the repeated fault caused by pair n of roll units can be determined using the equation $$P_n = p d_n (1+s_n),$$

in which p is the cycle of the repeated fault, $d_n$ is the roll diameter and $s_n$ is the slide in the pair of roll units in question.

The method for identifying repeated patterns is applicable to various different manufacturing processes of strip-like products, such as the manufacture of cold- or hot-rolled stainless steel, the manufacture of aluminum or copper band, and the manufacture of paper and board.

BRIEF DESCRIPTION OF THE DRAWINGS

In the following the invention will be described in more detail with the help of certain embodiments by referring to the enclosed drawings, where.

DETAILED DESCRIPTION

Figure 1:
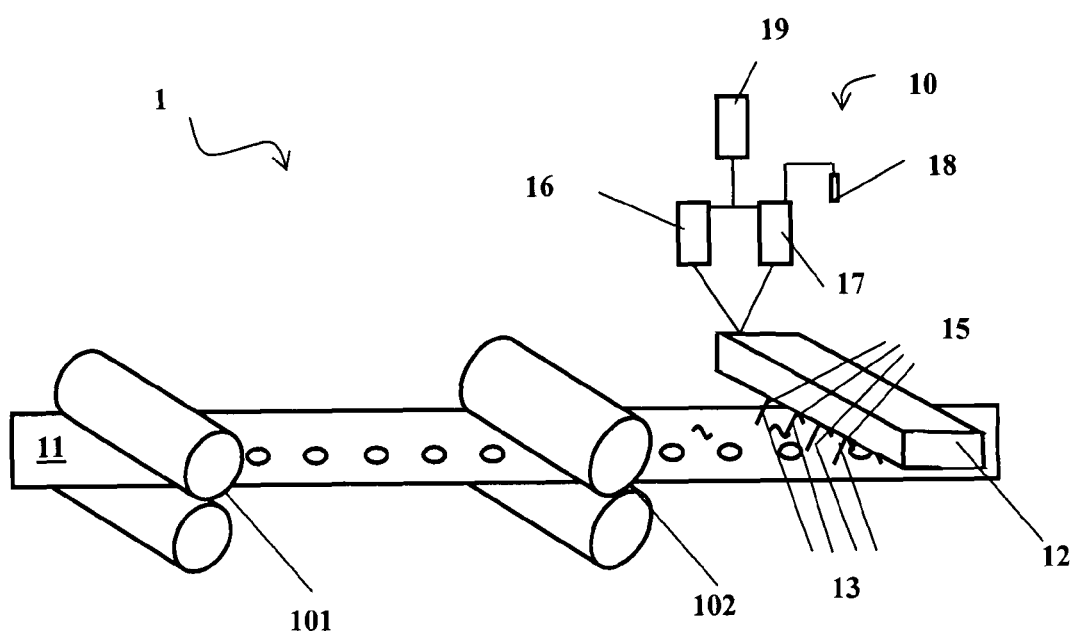
FIG. 1 is a general picture of a visual inspection system.

FIG. 1 illustrates an industrial application of a visual inspection system 10 including apparatus for identifying repeated faults in a strip-like product. The method for identifying repeated faults in a strip-like product can be used in this application. In this example the visual inspection system represents any visual system that takes and collects electronic images of different materials or objects for the purpose of categorizing their properties. The visual inspection system 10 is applicable to various types of continuous and discontinuous production lines. FIG. 1 illustrates an inspection system 1 for hot-rolled steel in which the visual inspection system 10 inspects a moving and continuous metal band 11 manufactured on the rolling process line.

The moving metal band 11 is inspected by one or more cameras 13 on one side of the metal band. The cameras 13 are fitted to a suitable mechanical support, such as a camera bar 12. The surface is inspected by reflected light; the lighting angle can be specular or scattered in relation to the camera viewing angle.

The cameras 13 can be any type of electronic cameras that can be directly or indirectly connected to an image processing unit 15. The functions of the image processing unit 15 can also be integrated with the camera 13, in which case the camera 13 is a more complex and independent image processing unit. The image signal from an analogue camera, such as an analogue CCD line or matrix camera, must first be converted into a digital form. The image data produced by a digital camera is usually better suited for digital processing in the image processing unit 15. The image processing unit 15 receives from the cameras 13 a digital representation of the view imaged by the cameras 13. The representation is in the form of a series of digital numbers. The image processing unit 15 interprets the material as an electronic image, referred to as an image elsewhere in this context, on the basis of information it has about the properties of the camera 13. For example, the image processing unit 15 combines the sequential data series sent by a line camera into a matrix that represents an image of the metal band 11.

The image processing unit 15 is a separate unit of equipment that is usually programmable. It can be partially or fully integrated in the camera as illustrated in FIG. 1. It can also be a personal computer or some other computer of a common type. One computer carries out the processing of image material from one or more cameras. The final product of this stage of processing is a set of electronic images representing selected parts of the band. The images are electronically manipulated to fulfill the requirements of the application at hand.

The images are forwarded to the next stage of processing, image analysis. This stage can be carried out using a separate computer that can be the workstation 16 within the visual inspection system 10 and that is usually shared between all of the cameras 13. Image analysis comprises tasks such as segmentation that can be used to find interesting areas, such as faults, in the image. After segmentation, characteristic components describing the properties of the areas found in segmentation can be collected. Characteristic components are numerical values that can be used for the identification—that is, categorisation—of areas.

The workstation 16 includes the user interface for the visual inspection system 10. It is used for the entry of different control parameters and the selection of desired views and reports that may indicate the state of the system and the quality of the inspected products, for example. The visual inspection system 10 naturally requires separate means for supplying power to the system and equipment for connecting with external systems, such as the actual process. These means, which are obvious to a person skilled in the art, can be located in an electrical cabinet 17. In addition to the workstation 16, external devices 18 can be used that provide warnings to the operator.

The image material is stored in an image database. The collection of images in the database consists of different types of digitized images of metal band faults. The faults are detected and the images digitized from moving metal band. The digital line cameras acquire images by light reflected from the faults, and the images are stored in the image database together with a set of calculated characteristics associated with certain areas of the image. A collection of several fault images each with a varying number of faults and associated characteristics constitutes a fault image collection. The associated characteristics can be used for the categorization of faults as desired by using a classifier 19.

It is visible in FIG. 1 that round spots (projections) appear in the metal band 11 after the pair of roll units 101, and dents resembling the letter Z appear after the pair of roll units 102. The circumference of the rolls 101 is smaller than that of the rolls 102.

Figure 2:
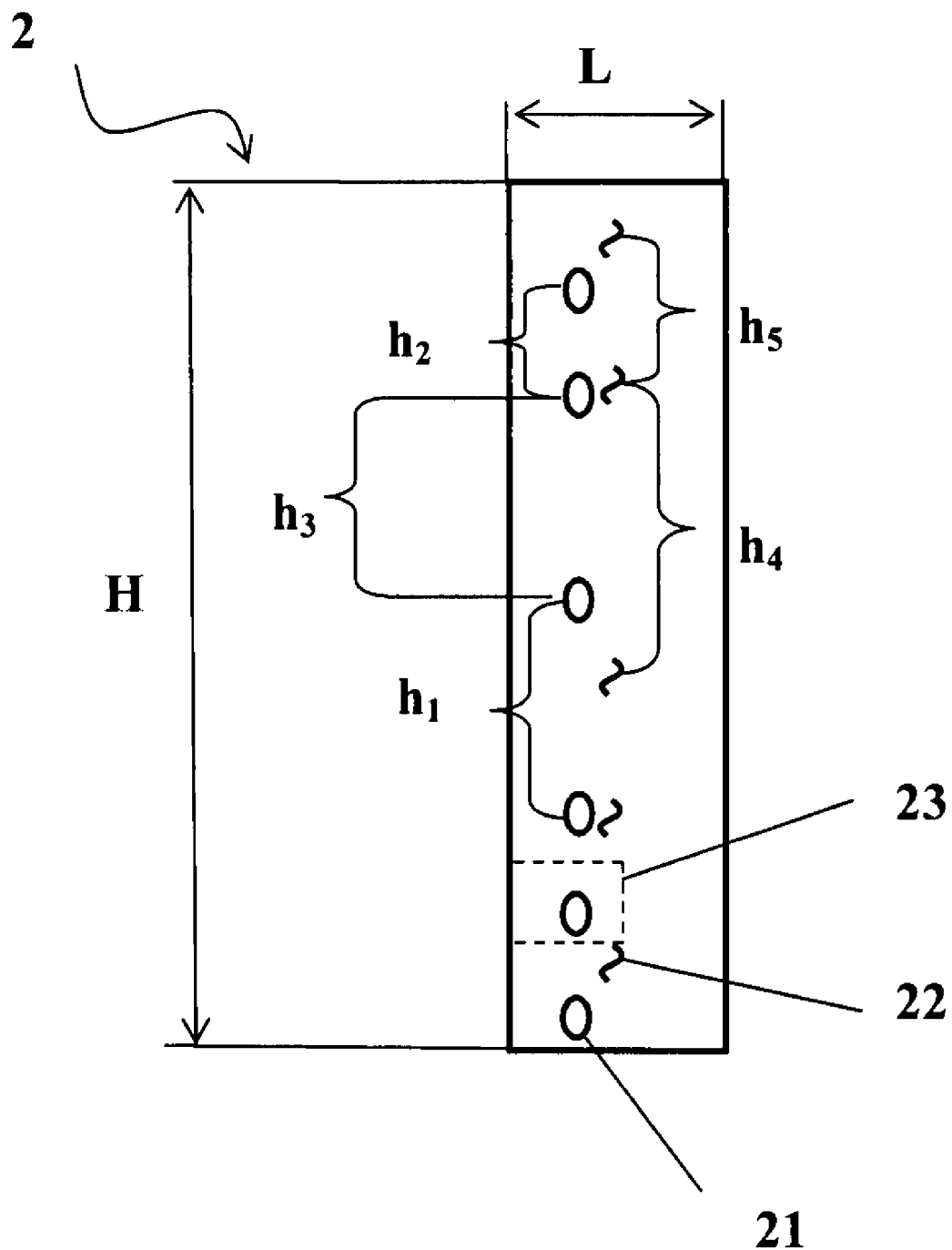
FIG. 2 illustrates a long image in the identification of a repeated pattern.

FIG. 2 illustrates a long image 2 used for the identification of a repeated pattern. The image 2 has been taken of the metal band 11 in FIG. 1 after the roll unit pairs 101 and 102 using one camera 13. There are four cameras in FIG. 1, and one camera is examined at a time. The width of the metal band is 1 m, and the width L of the image being examined is 0.3 m. The length H of the image 2 is 6 m. The circumference of the rolls 101 is 1.5 m and the circumference of the rolls 102 is 1.8 m.

Figure 3:
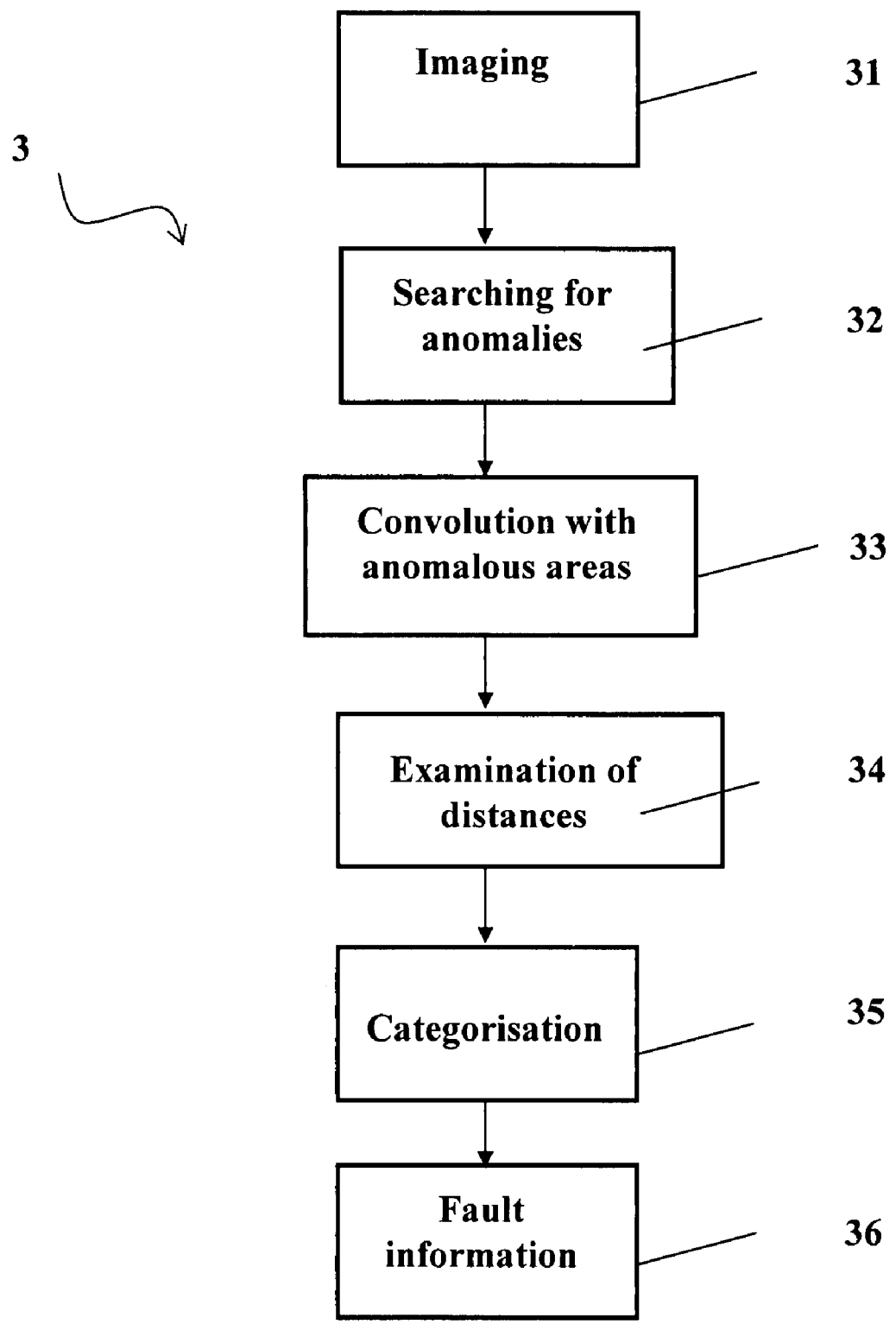
FIG. 3 is a block diagram of the method for identifying repeated faults combined with the determination of fault type, place and location.

FIG. 3 illustrates a block diagram 3 of the method for identifying repeated faults combined with the determination of fault type, place and location. At the first phase 31 of the method a digital image of the object being examined is created. The length of the image is determined on the basis of the object so that several occurrences of a fault can be included in the image. FIG. 2 illustrates a long image that accommodates three revolutions of the roll and thus may include three occurrences of a fault.

At the next phase 32 all anomalies are searched for in the image created of the object. An anomalous pixel is defined as a pixel that is too dark or too light compared with the average brightness of the image, for example. A binary image is created in which adjacent anomalous pixels neighboring each other in 8 directions constitute uniform anomalous areas. Thus the binary image may or may not include anomalous areas. The image may include a potentially high number of anomalous areas, and each of these is selected as a suspected repeated fault in turn. A search image surrounding the anomalous area is then created for each suspected repeated fault. The binary image shows the faults 21 and 22 of FIG. 2 as anomalous areas.

Figure 4:
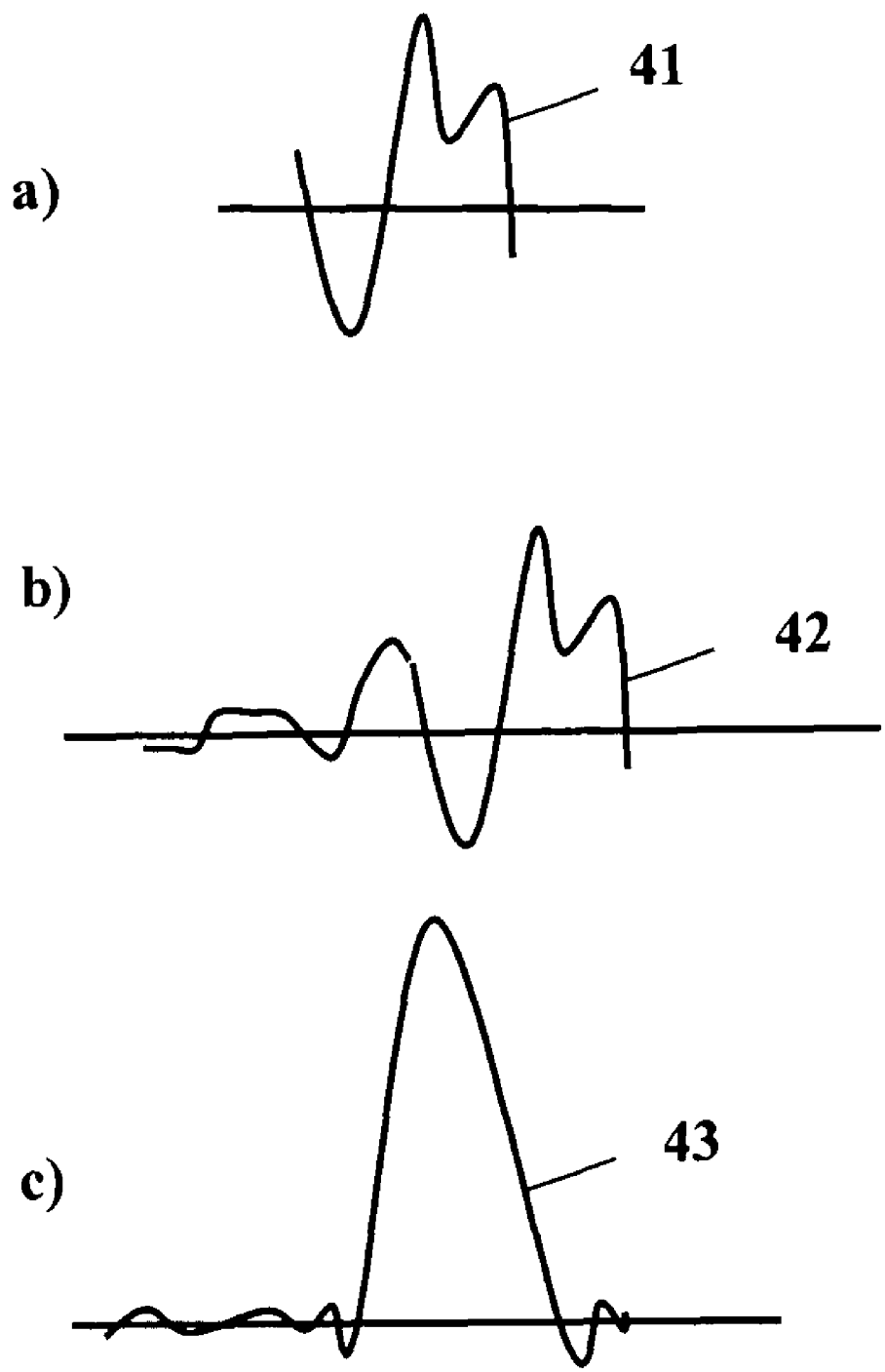
FIG. 4 illustrates the search image signal, the image signal being examined and the response image signal.
Figure 5:
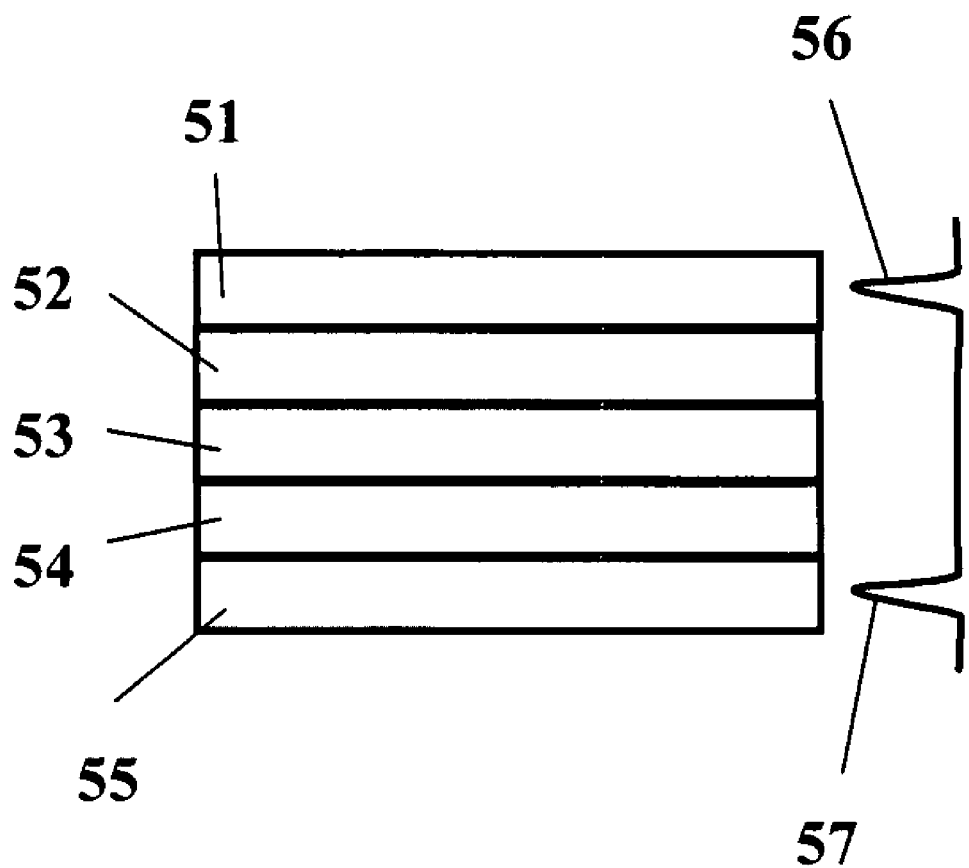
FIG. 5 illustrates the search of similar areas in the response image signal.

At phase 33 convolution is carried out using the search image of the anomalous area. Similar anomalies are searched for at each location in the cross direction. The search image representing the anomalous area is used to convolute the image signal in the longitudinal direction of the strip-like product—that is, in the machine direction. An area—also known as the search image—cut from the image is slid in the machine direction and slightly in the cross direction, searching for areas that are as similar to the cut area as possible. In FIG. 2 the area delimited by dotted lines is the search image 23. The search image signal 41 is presented in FIG. 4a. Slight sliding in the cross direction allows the track to move during imaging, for example. The similarity measure can be any correlation measure between the original finding and the other sections. A correlation measure can be comprised of the derivatives of convolution using different normalization factors. The final result of convolution filtering is a response image in which areas similar to the search image produce a high value. The image signal 42 being examined and the response image signal 43 are presented in FIGS. 4a and 4c. Similar areas can be searched and selected, for example, by selecting the 50 highest peaks in the response image—that is, the 50 highest values and their neighborhood so that each selected location includes only one value influencing the selection, and high values in the neighborhood are interpreted as being associated with the same finding or peak. FIG. 5 illustrates five rows of pixels 51-55 in which the peaks 56, 57 in the response image match the first row of pixels 51 and the fifth row of pixels 55. These are areas similar to the search image 23. Once convolution with the anomalous areas and the selection of similar areas has been completed, repeated fault areas have been found and marked.

At phase 34 the distances between the found fault areas are examined. The distances between sequential fault areas in the same cross-directional section are calculated. The distance is calculated in the longitudinal direction of the strip-like product (the machine direction), and the same cross-directional section refers to the area within which the search image has been slid in the longitudinal and cross directions at phase 33. In FIG. 2 two different distances $h_1$ and $h_2$ have been calculated as the distances between the round spots 21. Two different distances $h_4$ and $h_5$ have been calculated as the distances between the dents 22 resembling the letter Z. In practice the lengths of calculated distance lines vary between 0.3 and 30 m, for example, so it is feasible to interpret distance lines as having equal lengths within a tolerance of ±1 . . . 5%. On the other hand, the web or band can move between the edge guides in the cross direction. In this case distance lines located within ±1 cm in the cross direction of a web having a width of 1 m can be interpreted as being close enough to constitute distance lines of the same fault.

Once the distances in the longitudinal direction of a strip-like product have been calculated, their regularity is examined, taking into account the multiples of the distances—that is, 1× distance, 2× distance, etc. As all repeated fault areas have not necessarily been detected, multiples of the shortest distance are valid because one or more fault areas can be missing in between.

In FIG. 2 the distances between the round spots 21 have been calculated. Two different distances have been detected, and two fault pairs have been formed of them.

The distances for two fault pairs are $h_1$ and $h_2$, of which $h_1$ is a multiple of the shortest distance $h_2$—in other words, $h_1=2\times h_2$. The distance between the fault pairs $h_3$ is also a multiple of the shortest distance $h_2$—in other words, $h_3=2\times h_2$. In this case the repeating interval $P_{final}$ of the fault, the round spot 21, is $h_2$.

In FIG. 2 the distances between the dents 22 resembling the letter Z have been calculated. Two different distances have been detected, and two fault pairs have been formed of them. The distances for two fault pairs are $h_4$ and $h_5$, of which $h_4$ is a multiple of the shortest distance $h_5$—in other words, $h_4=2\times h_5$. The fault pairs are successive, meaning that their mutual distance is zero. In this case the repeating interval $P_{final}$ of the fault, the dent 22 resembling the letter Z, is $h_5$.

When inspecting watermarked paper or printed adhesive paper, for example, a missing regularly repeated pattern is searched for. When the distances are examined in this case, the length of a distance line between similar areas is not allowed to be a multiple of the most common parallel distance present in the image signal in the machine and/or cross direction because this means that one or more watermarks or imprints are missing between the areas at the ends of the distance line.

The fault is categorized at phase 35. The average appearance of the fault is determined with the help of a model image. An outline of the fault is drawn on the basis of the model image, and categorizing features such as area, elongation, average gray level, variance, roundness, border line length per area, etc., can be calculated for the outline.

When searching for regularly repeated faults at phase 36, a fault has a cycle, a location and a category. This information can be used for reporting or providing an alarm of an anomaly, or identifying the source of a fault, such as a failed roll. When information about the diameters of the working rolls and the amount of thinning at each pair of roll units is combined with the cycle of a repeated fault calculated at phase 34, the source of a detected repeated fault can be estimated using the following equation:

$$P_{final} = P_n \left(\frac{h_{1,F_{n+1}}}{h_{2,F_{n+1}}}\right)\left(\frac{h_{1,F_{n+2}}}{h_{2,F_{n+2}}}\right)\left(\frac{h_{1,F_{n+3}}}{h_{2,F_{n+3}}}\right)\cdots\left(\frac{h_{1,F_{n+i}}}{h_{2,F_{n+i}}}\right)$$
$$= P_n\left(\frac{h_{1,F_{n+1}} h_{1,F_{n+2}} h_{1,F_{n+3}} \cdots h_{1,F_{n+i}}}{h_{2,F_{n+1}} h_{2,F_{n+2}} h_{2,F_{n+3}} \cdots h_{2,F_{n+i}}}\right),$$

in which $P_{final}$ is the detected cycle of a repeated fault in the final product after going through i pairs of roll units, $P_n$ is the original cycle of the repeated fault caused by pair n of roll units, $h_{1,Fn+i}$ is the input thickness to the $i^{th}$ next pair of roll units and $h_{2,Fn+i}$ is the output thickness from the $i^{th}$ next pair of roll units. In other words, $h_{1,Fn+i}/h_{2,Fn+i}$ is the elongation in a pair of roll units.

The original cycle of the repeated fault caused by pair n of roll units can be determined using the equation $$P_n = pd_n(1+s_n),$$

in which p is the cycle of the repeated fault, $d_n$ is the roll diameter and $s_n$ is the slide in the pair of roll units in question. Thus the pair of roll units 101 illustrated in FIG. 1 can be determined as being the cause of the round spots 21, while the pair of roll units 102 illustrated in FIG. 1 can be determined as being the cause of the dents 22 resembling the letter Z.

In the above the invention has been described with the help of certain embodiments. However, the description should not be considered as limiting the scope of patent protection; the embodiments of the invention may vary within the scope of the following claims.

What is claimed is:

1. A method for identifying repeated patterns in a strip-like product, the method comprising:
    observing the strip-like product by at least one camera;
    creating at least one digital image signal comprised of pixels for examination;
    searching for an anomaly comprised of one or more pixels in the image signal;
    creating a search image of any detected anomaly and its neighbourhood;
    using the search image to convolute the image signal being examined and creating a response image signal;
    using said created response image signal to determine image areas within the image signal being examined that are substantially similar to the search image;
    calculating distance lines between substantially similar image areas in the cross and longitudinal directions of the strip-like product;
    comparing the distance lines with each other and substantially longitudinal distance lines of substantially equal length and/or selecting substantially longitudinal distance lines having lengths that are substantially multiples of each other from among the distance lines;
    creating one or more pairs of distance lines from the selected distance lines, each of said pair of distance lines respectively consisting of two longitudinal distance lines; and
    selecting pairs of distance lines from among the created pairs so that the distance between the pairs of distance lines is substantially a multiple of the longitudinal length of the shorter distance line in the pair and the distance lines in the pairs are substantially close to each other in the cross direction of the strip-like product.

2. A method according to claim 1, wherein the longitudinal length of the shorter distance line in the selected pair of distance lines is used to determine the diameter of the roll causing a regularly repeated anomaly in the image signal or image.

3. The method according to claim 2, wherein the strip-like product is a metal band.

4. The method according to claim 1, wherein the strip-like product is a metal band.

5. A method for identifying repeated patterns in a strip-like product, the method comprising:
    observing the strip-like product by at least one camera;
    creating at least one digital image signal comprised of pixels for examination;
    searching for an anomaly comprised of one or more pixels in the image signal;
    creating a search image of any detected anomaly and its neighbourhood;
    using the search image to convolute the image signal being examined and creating a response image signal;
    using said created response image signal to determine image areas within the image signal being examined that are substantially similar to the search image;
    calculating distance lines between substantially similar image areas substantially aligned in the longitudinal or cross direction in the cross and longitudinal direction of a strip-like product;

comparing the distance lines with each other and the most commonly present cross-directional and longitudinal distance lines, and selecting cross-directional distance lines having lengths that are substantially multiples of the most commonly present cross-directional distance lines, as well as longitudinal distance lines having lengths that are substantially multiples of the most commonly present longitudinal distance lines; and selecting multiples of distance lines having a multiplier of at least two from among the selected distance lines.

6. A method according to claim 5, wherein the strip-like product is watermarked paper.

7. An apparatus for identifying repeated patterns in a strip-like product in which apparatus the strip-like product is observed by at least one camera and at least one digital image signal comprised of pixels is created for examination, wherein the apparatus includes:

means for searching for an anomaly comprised of one or more pixels in the image signal;

means for creating a search image of any detected anomaly and its neighbourhood;

means for convoluting the image signal being examined using the search image;

means for creating a response image signal from the convolution; and means for determining image areas within the image signal being examined that are substantially similar to the search image using the response image signal;

means for calculating distance lines between substantially similar image areas in the cross and longitudinal directions of the strip-like product;

means for comparing the distance lines with each other;

means for selecting distance lines of substantially equal length and/or distance lines having lengths that are substantially multiples of each other from among the distance lines;

means for creating one or more pairs of distance lines from the selected distance lines, each of said pair of distance lines respectively consisting of two longitudinal distance lines; and means for selecting pairs of distance lines from among the created pairs of distance lines so that the distance between the pairs of distance lines is substantially a multiple of the longitudinal length of the shorter distance line in the pair of distance lines and the distance lines in the pairs of distance lines are substantially close to each other in the cross direction of the strip-like product.

8. An apparatus according to claim 7, wherein the apparatus includes means for using the longitudinal length of the shorter distance line in the selected pair of distance lines to determine the diameter of the roll causing a regularly repeated anomaly in the image signal or image.

9. An apparatus for identifying repeated patterns in a strip-like product in which apparatus the strip-like product is observed by at least one camera and at least one digital image signal comprised of pixels is created for examination, wherein the apparatus includes:

means for searching for an anomaly comprised of one or more pixels in the image signal;

means for creating a search image of any detected anomaly and its neighbourhood;

means for convoluting the image signal being examined using the search image;

means for creating a response image signal from the convolution; and means for determining image areas within the image signal being examined that are substantially similar to the search image using the response image signal;

means for calculating distance lines between substantially similar image areas substantially aligned in the longitudinal or cross direction in the cross and longitudinal direction of a strip-like product;

means for comparing the distance lines with each other;

means for selecting the most commonly present cross-directional and longitudinal distance lines, cross-directional distance lines having lengths that are substantially multiples of the most commonly present cross-directional distance lines, as well as longitudinal distance lines having lengths that are substantially multiples of the most commonly present longitudinal distance lines from among the distance lines; and means for selecting multiples of distance lines having a multiplier of at least two from among the selected distance lines.

* * * * *